United States Patent
Schulte et al.

(10) Patent No.: US 9,056,726 B2
(45) Date of Patent: Jun. 16, 2015

(54) DEVICE AND METHOD FOR GROUPING ARTICLES

(75) Inventors: Josef Schulte, Aschendorf (DE);
Andreas Prahm, Barßel (DE); Björn Brandhorst, Hörstel (DE)

(73) Assignee: Focke & Co. (GmbH & Co. KG), Verden (DE)

( * ) Notice: Subject to any disclaimer, the term of this patent is extended or adjusted under 35 U.S.C. 154(b) by 0 days.

(21) Appl. No.: 14/127,769

(22) PCT Filed: May 18, 2012

(86) PCT No.: PCT/EP2012/002132
§ 371 (c)(1),
(2), (4) Date: Feb. 5, 2014

(87) PCT Pub. No.: WO2013/000527
PCT Pub. Date: Jan. 3, 2013

(65) Prior Publication Data
US 2014/0151188 A1 Jun. 5, 2014

(30) Foreign Application Priority Data
Jun. 27, 2011 (DE) .......................... 10 2011 105 887

(51) Int. Cl.
*B65G 37/00* (2006.01)
*B65G 47/53* (2006.01)
(Continued)

(52) U.S. Cl.
CPC .............. *B65G 37/00* (2013.01); *B65B 25/141* (2013.01); *B65G 47/082* (2013.01); *B65H 33/18* (2013.01);
(Continued)

(58) Field of Classification Search
None
See application file for complete search history.

(56) References Cited

U.S. PATENT DOCUMENTS 5,897,291 A    4/1999   Gerwe
6,644,461 B1   11/2003  Imbert
(Continued)

FOREIGN PATENT DOCUMENTS

DE    29809215 U1   9/1998
DE    19749985 A1   5/1999
(Continued)

OTHER PUBLICATIONS

Deutsches Patent-Und Markenamt, Recherchebericht, German Patent and Trademark Office Search Report for the priority German patent application.
(Continued)

*Primary Examiner* — Kavel Singh
(74) *Attorney, Agent, or Firm* — Laurence P. Colton; Smith Risley Tempel Santos LLC

(57) ABSTRACT

The invention relates to a device for grouping (flat) articles (10), in particular hygiene products such as diapers, wherein the articles (10) to be grouped are conveyable individually and one after another on a feed conveyor (19) and are suppliable to a grouping conveyor (12). The invention is characterized in that the grouping conveyor (12) has compartments (13) for in each case one group (11) of articles (10), in which compartments the articles (10) are arranged preferably standing upright, in particular tightly packed together, wherein the articles (10) are suppliable by means of the feed conveyor (19) at an angle, in particular substantially transversely, with respect to the conveying direction of the grouping conveyor (12) and are conveyable in the conveying direction of the grouping conveyor (12) by way of a substantially cone-shaped conveyor (24) thus forming a group (11) of articles (10) in one compartment (13).

16 Claims, 3 Drawing Sheets

(51) Int. Cl.
*B65G 47/08* (2006.01)
*B65H 33/18* (2006.01)
*B65H 29/22* (2006.01)
*B65H 31/06* (2006.01)
*B65H 31/26* (2006.01)
*B65H 31/30* (2006.01)
*A61F 13/15* (2006.01)
*B65B 25/14* (2006.01)

(52) U.S. Cl.
CPC ... *B65H 2301/321* (2013.01); *B65H 2301/4474* (2013.01); *B65H 2701/1924* (2013.01); *B65G 47/53* (2013.01); *B65H 29/22* (2013.01); *B65H 31/06* (2013.01); *B65H 31/26* (2013.01); *B65H 31/3072* (2013.01); *B65H 2301/4214* (2013.01); *B65H 2301/4461* (2013.01); *B65H 2301/4476* (2013.01); *B65H 2301/4477* (2013.01); *B65H 2404/1118* (2013.01); *B65H 2404/1315* (2013.01); *B65H 2404/741* (2013.01); *B65H 2404/742* (2013.01); *B65H 2406/32* (2013.01); *A61F 13/15764* (2013.01)

(56) References Cited

U.S. PATENT DOCUMENTS

| | | | |
|---|---|---|---|
| 6,729,617 | B1 | 5/2004 | Chaume |
| 2007/0216082 | A1* | 9/2007 | Fenile et al. ............. 271/69 |
| 2010/0071318 | A1* | 3/2010 | Brandhorst et al. ......... 53/446 |

FOREIGN PATENT DOCUMENTS

| | | |
|---|---|---|
| DE | 102006045087 A1 | 3/2008 |
| EP | 1050494 A1 | 11/2000 |
| EP | 0958207 B1 | 1/2002 |
| EP | 1194249 B1 | 12/2004 |
| EP | 1557360 A1 | 7/2005 |
| EP | 1681250 A1 | 7/2006 |
| EP | 2165934 A2 | 3/2010 |
| GB | 2454166 A | 5/2009 |

OTHER PUBLICATIONS

State Intellectual Property Office of the People's Republic of China, Search Report (on related application CN201280037031.3), Jan. 20, 2015.

* cited by examiner

DEVICE AND METHOD FOR GROUPING ARTICLES

The application is the US PCT National Phase of International Application No. PCT/EP2012/002132 having an International Filing Date of 18 May 2012, which claims priority on German Patent Application No. 10 2011 105 887.0 having a filing date of 27 Jun. 2011.

The invention relates to a device for grouping (flat) articles, in particular hygiene products such as diapers, wherein the articles to be grouped are conveyable individually and one after another on a feed conveyor and are suppliable to a grouping conveyor, as claimed in the preamble of claim 1. In addition, the invention relates to a corresponding method as claimed in the preamble of claim 13.

In practice, it is usual for the articles to be grouped to be conveyed individually and spaced apart from one another on a feed conveyor and to be transferred from said feed conveyor into a connecting (grouping) conveyor with compartments for the articles. The grouping conveyor can, for example, be a compartment conveyor with several compartments for, in each case, one article. Further along the operation, several articles are then pushed out of the compartment conveyor thus forming a group.

A disadvantage of these types of solutions is the very large amount of space required for the compartment conveyor. In a disadvantageous manner, the large dimensions of the compartment conveyor force a correspondingly adapted layout for the packaging line.

A further disadvantage is that as a result of the large dimensions of the compartment conveyor, the individual stations inside the packaging line are only accessible with difficulty in the event of faults. In addition, known compartment conveyors can only be converted at great expense such that they can only be used in a restricted manner for articles of different sizes.

Proceeding from here, the object underlying the invention is to develop further devices and methods of the type mentioned in the introduction, in particular with regard to requiring as little space as possible.

To achieve said object, a device as claimed in the invention has the features of claim 1. It is accordingly provided that the grouping conveyor has compartments for in each case one group of articles, in which compartments the articles are arranged preferably standing upright, in particular tightly packed together, wherein the articles are suppliable by means of the feed conveyor at an angle, in particular substantially transversely, with respect to the conveying direction of the grouping conveyor and are conveyable in the conveying direction of the grouping conveyor by way of a substantially cone-shaped conveyor thus forming a group of articles in one compartment.

A characteristic of the invention can consist in the use of a special conveyor with a substantially (truncated)-cone-shaped form. The conveyor can be rotatingly drivable, the articles, when being conveyed by the conveyor, sitting in the region of an outside surface of the conveyor.

A further characteristic can consist in the spatial arrangement of the conveyor, namely that the conveyor is rotatingly driveable about an upright axis of rotation, wherein the axis of rotation is inclined with respect to the vertical about two axes in such a manner that the region of the outside surface, against which the articles abut for conveying, is directed substantially transversely, in particular vertically, with respect to the conveying path of the articles and the conveying path of the articles extends substantially tangentially with respect to the outside surface of the conveyor. In this way, the articles to be conveyed and the circumferential face of the conveyor are aligned in an optimum manner with respect to one another.

As claimed in an advantageous further development of the invention, it is provided that the axis of rotation is arranged in an eccentric manner and/or in that the radius of the conveyor varies over the circumference in such a manner that, when the conveyor rotates, the articles are conveyable at an angle, in particular transversely, with respect to the conveying direction of the feed conveyor or substantially in the conveying direction of the grouping conveyor.

As a result of the structural characteristics, the conveyor forwards the articles not only in the conveying direction on the feed conveyor, but also at an angle, in particular transversely, with respect hereto in the conveying direction of the grouping conveyor. The conveyor consequently serves for conveying the articles in two directions in a (horizontal) plane of the grouping conveyor.

A further characteristic of the invention can consist in that a device for delivering an air flow which acts on the articles laterally in the conveying direction of the grouping conveyor is positioned in the operating region of the conveyor, in particular a blowing device. The blowing device can fulfill several purposes. On the one hand, it can support when the articles are conveyed in the conveying direction of the grouping conveyor. On the other hand, it can act to prevent articles already located in the compartments tipping up. Such an event threatens in particular when the compartments are not yet fully filled, that is during the filling operation or when a compartment can or is only to be filled in part.

Realizing some elements of the grouping conveyor to act upon the articles with negative pressure is also advantageous. In this way, the articles can be prevented from not remaining in the provided position on the grouping conveyor when they are being conveyed on the grouping conveyor or at least actions against such behavior can be taken.

In a structural regard, one characteristic provides that the compartments formed on the grouping conveyor are defined by entrainment means of the conveyor run, wherein the articles project beyond the top surface of the entrainment means and the conveyor is arranged above the entrainment means for conveying the articles. It is preferably provided, in addition, that a top surface of the entrainment means is realized so as to be inclined in a descending manner on the grouping conveyor in opposition to the direction in which the articles are supplied. In this way, the articles can be prevented from colliding with the entrainment means and consequently blocking the feed.

A method as claimed in the invention has the features of claim 13. It is accordingly provided that the grouping conveyor has compartments for in each case one group of articles, in which compartments the articles are arranged preferably standing upright, in particular tightly packed together, wherein the articles are supplied by means of the feed conveyor at an angle, in particular substantially transversely, with respect to the conveying direction of the grouping conveyor and are conveyed in the conveying direction of the grouping conveyor by way of a substantially cone-shaped conveyor thus forming a group of articles in one compartment.

Further details of the method as claimed in the invention or of the device as claimed in the invention can be found, moreover, in the sub-claims and the description.

A preferred exemplary embodiment of the invention is described below by way of the drawings, in which.

FIG. 4 and

Figure 3:
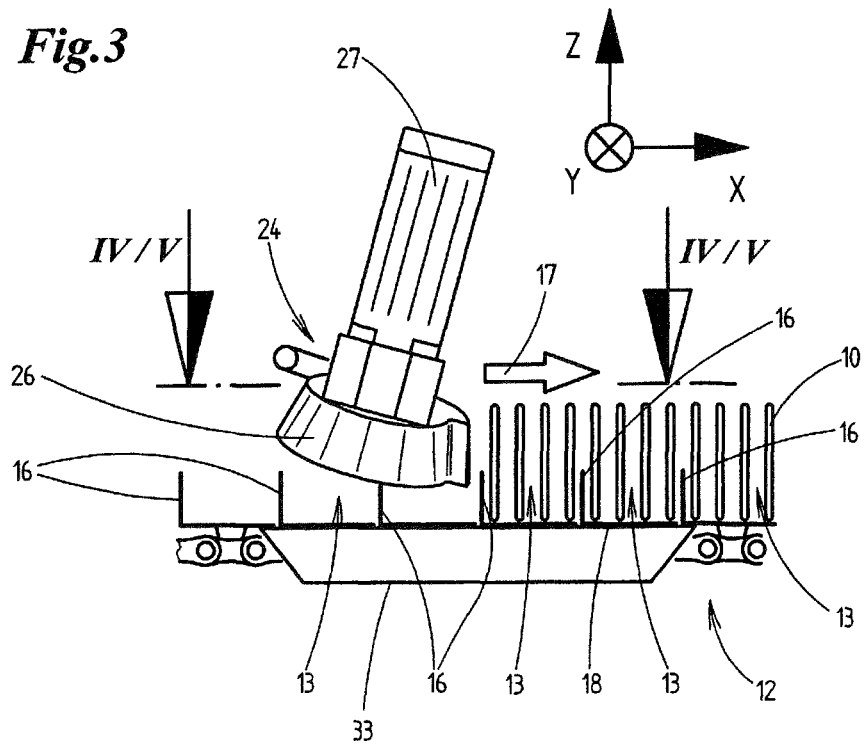
FIG. 3 shows a vertical section through the device along the line of intersection III-III in FIG. 1.
Figure 5:
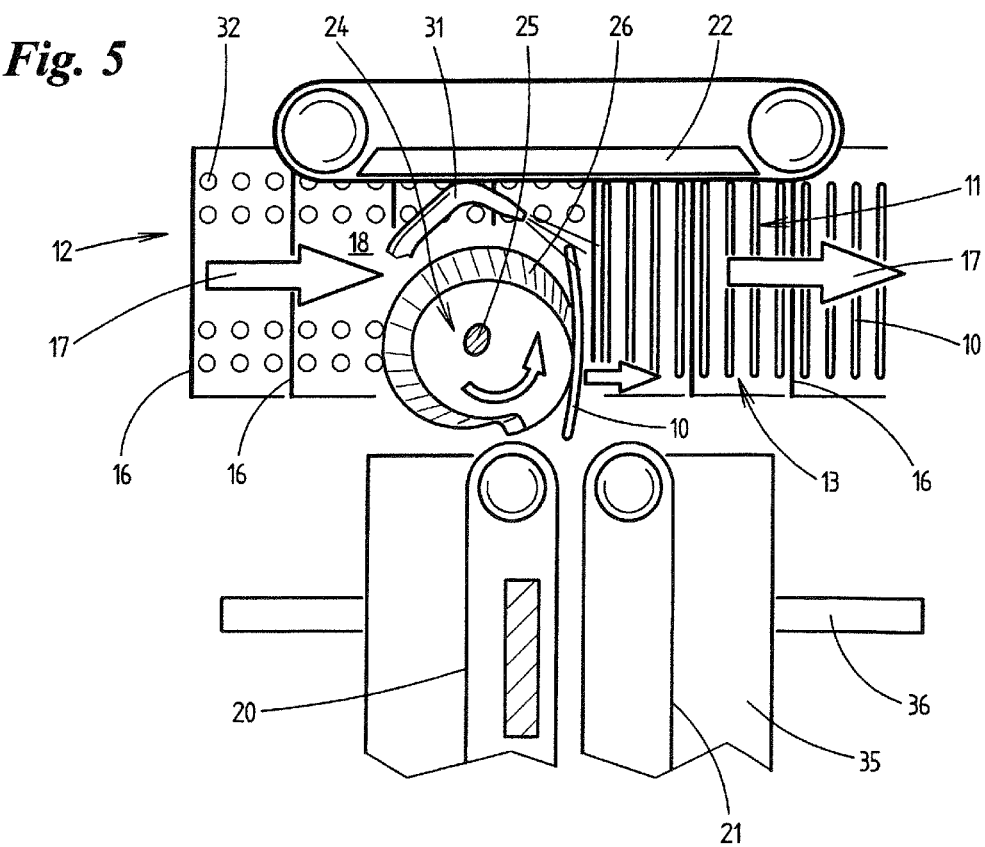

FIG. 5 show a horizontal section through the device along the line of intersection IV-IV in FIG. 3 during different phases of the grouping operation.

The invention is described below by way of a device for grouping articles 10. The articles 10 can be (packaged) hygiene products such as diapers, napkins or cleansing cloths.

In the present case, the articles 10 have a flat form and, by means of the device, are combined to form a product group 11. The articles 10, tightly packed together, abut against one another inside the product group 11 by way of large-area front or rear sides.

The device described below can be part of a packaging line or production line for the articles 10. However, only the regions of the line which are important to the grouping operation are described.

A grouping conveyor 12 is a central member of the device. The grouping conveyor 12 has consecutive compartments 13 for receiving in each case one product group 11 produced from articles 10.

In the present case, the grouping conveyor 12 is realized as an endless conveyor, having a conveyor run 14 which is guided by means of guide rollers 15. One or several of the guide rollers 15 can be driven by means of a corresponding drive 22. The drive 22 preferably operates in a continuous manner.

Entrainment means 16, which are arranged vertically or radially with respect to the conveyor run 14, are arranged spaced apart on the conveyor run 14. The compartments 13 are defined transversely with respect to the conveying direction of the grouping conveyor 12 by the entrainment means 16, two consecutive compartments 13 being separated from one another by a common entrainment means 16. The conveying direction of the grouping conveyor 12 is indicated by arrows 17.

The distance between two entrainment means 16 in the conveying direction of the grouping conveyor 12 corresponds to the corresponding width of the product group 11. The distance between the entrainment means 16 can also be chosen such that the product group 11 is slightly compressed.

The grouping of the articles 10 is effected in the region of a top run 18 of the grouping conveyor 12. A feed conveyor 19 is provided by way of which the articles 10 are conveyed individually and spaced apart in the conveying direction. The conveying direction of the feed conveyor 19 is aligned at an angle, in particular transversely, with respect to the grouping conveyor 12 such that the articles 10 can be inserted into the compartments 13 which are open at the side.

In the present case, the articles 10 are conveyed in the region of the feed conveyor 19 in the same relative position in which they are also arranged in the compartments 13 of the grouping conveyor 12. The articles 10 rest or stand with a narrow side on the top run 18 of the grouping conveyor 12. The articles 10 are supplied in a corresponding manner by the feed conveyor 19 in the same relative position and substantially at the same height.

In the region of the feed conveyor 19, the articles 10 are held on both sides by conveyor runs of endless conveyors 20, 21 which extend in parallel. The endless conveyors 20, 21 can be constructed such that another change in the relative position of the articles 10, in particular a rotation, is also performed in the region of the feed conveyor 19 before the articles 10 are transferred to the grouping conveyor 12 in the final relative position. The feed conveyor 19 is also driven, preferably continuously, by means of a drive (not shown).

The articles 10 are supplied individually into a compartment 13 on the top run 18 of the grouping conveyor 12 by the feed conveyor 19. The feed movement is defined by a stop means 23, against which the articles 10 collide by way of an end face and which extends laterally along the top run 18 pointing in the conveying direction.

The stop means 23, in the present case, is realized as an endless conveyor, a conveyor run 15 of the endless conveyor extending along a corresponding edge of the top run 18 and serving as a lateral stop for the articles 10. As a characteristic, the articles 10 can be acted upon with negative pressure in the region of the conveyor run 15. To this end, a suction box 22 extends along the conveyor run 15 on the side of the conveyor run 15 remote from the articles 10. The suction box 22 can be connected to a negative pressure source and set up for the purpose of generating negative pressure over the corresponding length of the conveyor run 15 on the side of the conveyor run 15 facing the articles 10. The conveyor run 15 can be set up in a manner corresponding hereto. In this way, the articles 10 are prevented from being flung back into the conveyor path as a result of striking too strongly against a lateral stop means.

A characteristic consists in a special conveyor 24 for conveying the articles 10 in the region of the supplying of the same to the grouping conveyor 12.

The conveyor 24 is rotatingly drivable about an upright axis 25 by means of a drive 27 and has an outer surface 26 which is aligned for conveying the articles 10 in a manner corresponding to the supplying of the same.

In the present case, the articles 10 are supplied standing upright and abutting tangentially against the outer surface 26 of the conveyor 24, as a result of which they are able to be forwarded in the conveying direction of the feed conveyor 19. In addition, the conveyor 24 is set up at the same time for conveying the articles 10 laterally in the conveying direction of the grouping conveyor 12. For this purpose, the conveyor 24 is realized in a cone-shaped manner, in particular in a truncated-cone-shaped manner, having the substantially upright, circumferential outer surface 26. For conveying the supplied articles 10 laterally, the cross section of the conveyor 24 is realized in an irregular manner, namely with a radius which alters over the circumference of the cross section. In this way, the articles 10, when abutting against the outer surface 26, are moved laterally in the conveying direction of the grouping conveyor 12 as a result of the increasing radius. The arrangement of the conveyor 24, in this case, can be chosen such that a product group 11, which is already located in a compartment 13 on the grouping conveyor 12, is compressed in the conveying direction.

The axis 25 of the conveyor 24, in the present case, is realized inclined with respect to the vertical in two directions such that, in the contact region with the articles 10 to be conveyed upright, the outer surface 26 is aligned parallel to said articles thus aligning the articles 10 tangentially with respect to the circumference of the conveyor 24.

Figure 4:
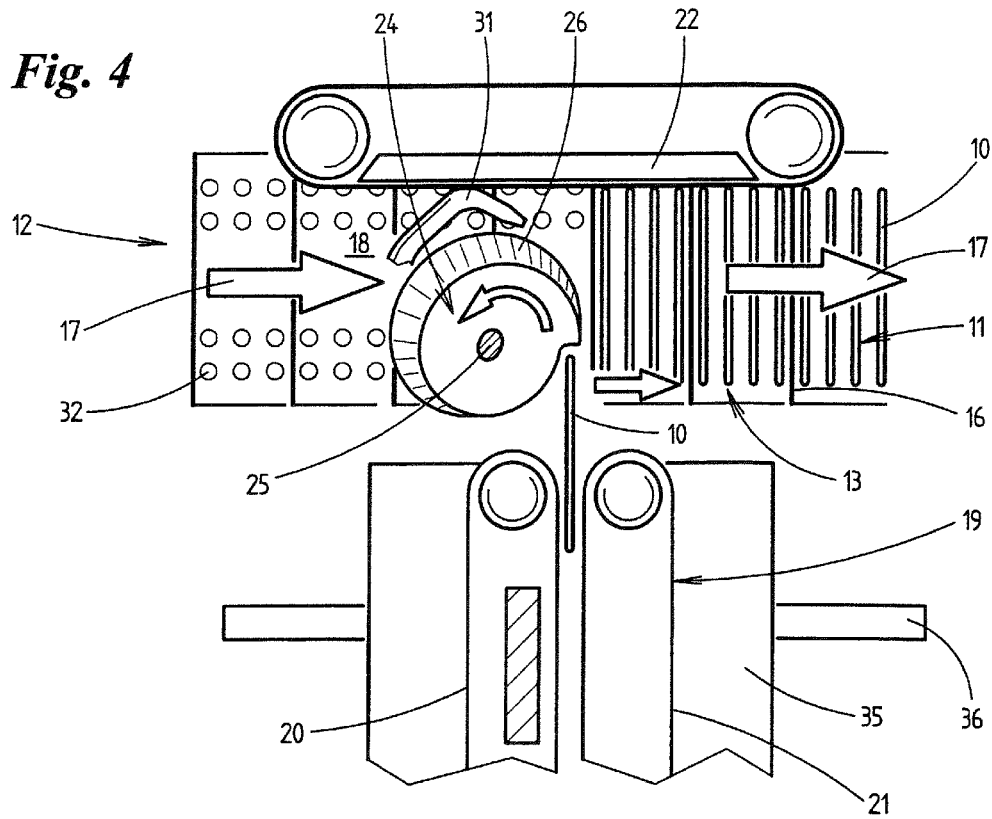

As already depicted, the radius of the conveyor 24 varies over the circumference of the same. The radius can alter continuously, that is first of all increase continuously and then decrease again to an initial radius. As an alternative to this, the radius, as in the present case, can increase continuously in order to then be reduced sharply or suddenly in the region of a shoulder. A shoulder 28 can be formed in the outside surface 26 in this way. The object of the shoulder 28 can consist in serving as a stop for the supplied articles 10. As an alternative to this, it is also conceivable for the shoulder 28 to serve the purpose of contributing to removing the articles 10 laterally in the conveying direction of the grouping conveyor 12. In the first case, it is conceivable for the rotational speed of the conveyor 24 to be slower than the speed at which the articles 10 are supplied such that the articles 10 are guided in a controlled manner at the edge which is formed by the shoulder 28 (FIG. 4). In the latter case, it is conceivable for the rotational speed of the conveyor 24 to be faster than the speed at which the articles 10 are supplied such that the articles 10 do not collide with the shoulder 28, but are accelerated laterally by said shoulder in the conveying direction of the grouping conveyor 10 (FIG. 5).

As an alternative to the described (truncated)-cone-shaped form of the conveyor 24, a cylindrical form of the same is also conceivable, wherein an eccentric axis of rotation would also make it possible for the articles 10 to be conveyed laterally.

Figure 2:
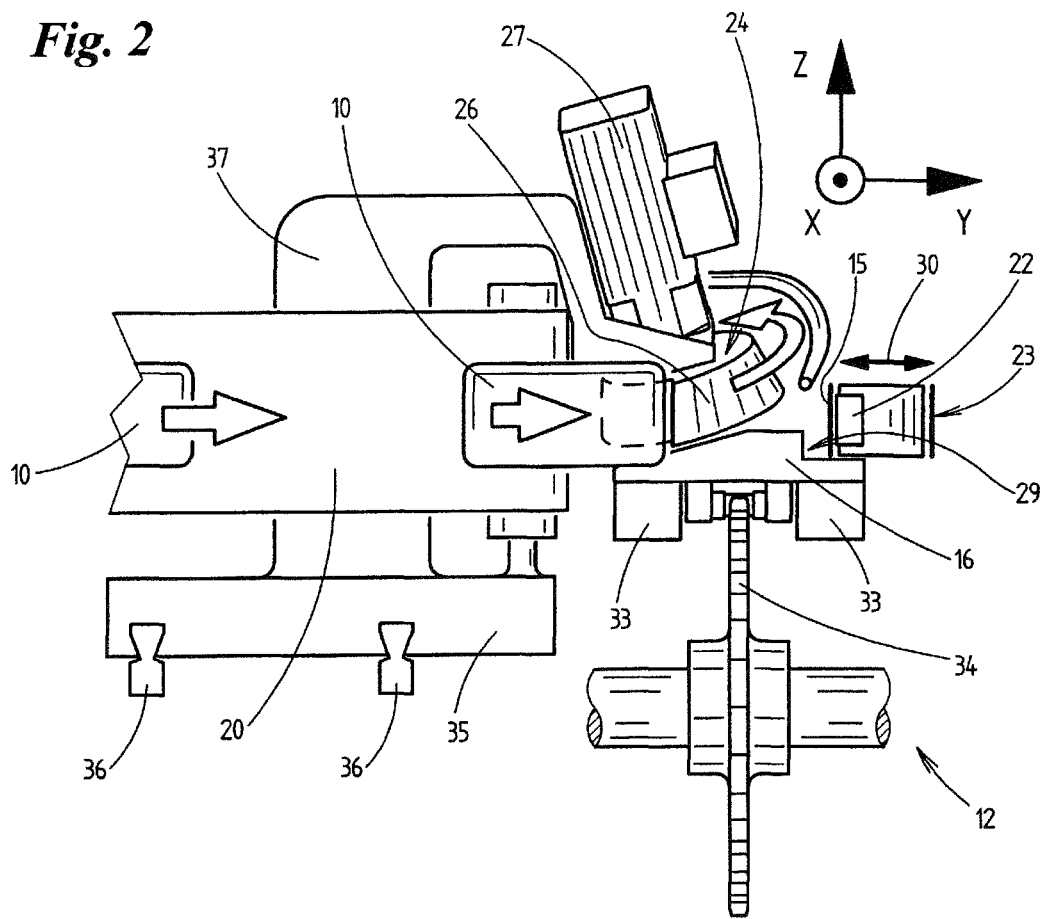
FIG. 2 shows a vertical section through the device along the line of intersection II-II in FIG. 1.

As can be seen from FIG. 2, the conveyor 24 is arranged above the entrainment means 16. In this case, the entrainment means 16 are adapted particularly to the alignment of the conveyor 24 with regard to their design. On the one hand, the top surface of the entrainment means 16 descends in the direction of the feed conveyor 19. The inclination of the rotational axis 25 is taken into consideration in this way. In this way, the height of the entrainment means 16 in the region of the supplying of the articles 10 is additionally so low that an unintended collision between the articles 10 and an entrainment means 16 does not bring about an obstruction of the feed in said region. Rather, the entrainment means 16 provide at best a stop edge which is small in such a manner that the articles 10 slide laterally past the entrainment means 16.

In addition, FIG. 2 shows that the height of the entrainment means 16 is (clearly) lower than the height of the articles 10 such that said articles can be conveyed by the conveyor 24 above the entrainment means 16.

In the region of the stop means 23, the entrainment means 16 also have a recess 29, in the region of which the conveyor run 15 or the suction box 22 extend. The distance of the stop means 23 with reference to a longitudinal center axis of the grouping conveyor 12 is realized so as to be adjustable corresponding to the double arrow 30 (FIG. 2).

Figure 1:
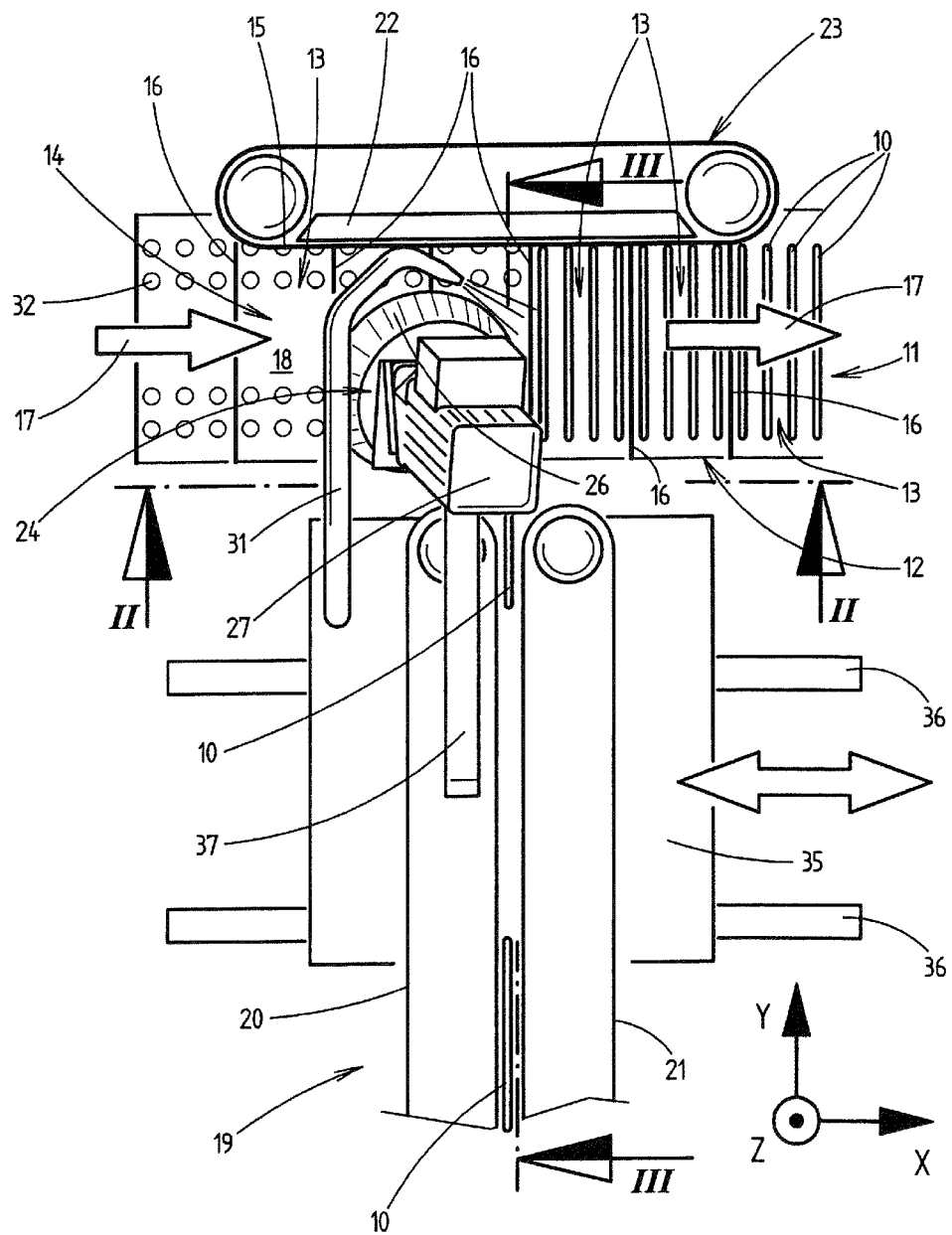
FIG. 1 shows a top view of a device for grouping articles.

The grouping of the articles 10 into at least one compartment 13 of the grouping conveyor 12 can be supported as a further characteristic by means of compressed air. To this end, a blowing device 31 is provided in the operating region of the conveyor 24. The blowing device 31 has a nozzle, through which compressed air is able to be blown laterally against the articles 10 which are located in the compartments 13 (FIG. 1). The articles 10 are protected from falling over in this way if, for example, the product group 11 does not fill out the compartment 13. A conceivable cause, for example, is a planned smaller product group 11 or a fault in the feeding of the articles 10. In addition, the blowing device 31 can also support a supplied article 10 being conveyed laterally by the conveyor 24 (FIG. 5).

To protect the position of the articles 10 on the top run 18 of the grouping conveyor 12, the entrainment means 16, on the one hand, contribute to defining the compartments 13 transversely with respect to the conveying direction of the grouping conveyor 12. In addition, the negative pressure exerted in the region of the stop means 23 onto the end faces of the articles contributes to this. A further contribution is effected by a corresponding negative pressure device in the region of the grouping conveyor 12. To this end, said grouping conveyor has openings 32 in the region of the top run 18, by means of which, as a result of suction boxes 33 arranged beneath the top run 18, the articles are sucked against the top run 18.

In the present case, the grouping conveyor 12 is realized as a pocket chain conveyor which also forms the entrainment means 16. The pocket chain drive 34 is guided below the top run 18, the suction boxes 33 extending in the longitudinal direction of the grouping conveyor 13 on both sides of the drive.

The feed conveyor 19, the conveyor 24 and the blowing device 31 are connected structurally to form one unit which is movable as one. The unit is mounted on a carriage 35 which is mounted so as to be movable laterally on rails 36, namely parallel to the conveying direction of the grouping conveyor 12. The conveyor 24 with the drive 27 is connected to the carriage 35 by means of a hoop 37. When no articles 10 are supplied to the grouping conveyor 12, the unit can be moved laterally in order to balance out the gaps in the conveyor flow.

Once a product group 11 is formed in a compartment 13, the product group 11 can be conveyed away from the compartment 13 of the grouping conveyor 12 by means of a pushing device (not shown). To this end, the pushing device 30 can have a slide which is movable at an angle, preferably transversely, with respect to the conveying direction of the grouping conveyor 12 in order to grasp a product group 11 through between two entrainment means 16 and push it away transversely from the grouping conveyor 12. Since the grouping conveyor 12 is driven continuously, the pushing movement of the slide can be superimposed on with a movement which points in the conveying direction of the grouping conveyor 12.

By means of a control means (not shown), the drives of the conveyor 24 (drive 27) and/or of the grouping conveyor 12 (drive 34) and/or of the slide (not shown) and/or of the pushing device are matched to one another.

LIST OF REFERENCES

10 Article
11 Product group
12 Grouping conveyor
13 Compartment
14 Conveyor run
15 Conveyor run (stop means)
16 Entrainment means
17 Arrow
18 Top run
19 Feed conveyor
20 Endless conveyor
21 Endless conveyor
22 Suction box
23 Stop means
24 Conveyor
25 Axis
26 Outer surface
27 Drive (conveyor)
28 Shoulder
29 Recess
30 Double arrow
31 Blowing device
32 Opening
33 Suction box
34 Box-type chain drive
35 Carriage
36 Rail
37 Hoop

The invention claimed is:

1. A device for grouping articles (10), in particular hygiene products such as diapers, wherein the articles (10) to be grouped are conveyable individually and one after another on the device, comprising:

a grouping conveyor (12) that having compartments (13) for in each case one group (11) of articles (10), in which compartments articles (10) are arranged standing upright;

a feed conveyor (19) for supplying articles (10) to the grouping conveyor (12) at an angle that is substantially transverse to the conveying direction of the grouping conveyor (12);

a substantially cone-shaped conveyor (24) for conveying articles (10) into the compartments (13) thus forming a group (11) of articles (10) in one each of the compartments (13), wherein the substantially cone-shaped conveyor (24) is mounted on the device at an angle whereby the substantially cone-shaped conveyor (24) is rotatingly drivable about an upright axis of rotation (25) that is inclined with respect to the vertical about two axes, whereby a portion of an outside surface (26) of the cone-shaped conveyor (24) against which articles (10) abut for conveying is directed substantially transversely with respect to the conveying path of articles (10) when conveying articles (10) into the compartments (13); and a feed conveyor (19) for supplying articles (10) to the grouping conveyor (12), whereby articles (10) are conveyed in the conveying direction of the grouping conveyor (12) within the compartments (13).

2. The device as claimed in claim 1, wherein, when being conveyed by the conveyor (24), articles (10) sit in the region of the outside surface (26) of the conveyor (21).

3. The device as claimed in claim 2, wherein the outside surface (26), against which the articles (10) abut for conveying, is directed vertically with respect to the conveying path of articles (10) and the conveying path of articles (10) extends substantially tangentially with respect to the outside surface (26) of the conveyor (24).

4. The device as claimed in claim 1, wherein at least one of (a) the axis of rotation (25) is arranged in an eccentric manner and (b) the radius of the conveyor (24) varies over the circumference in such a manner that, when the conveyor (24) rotates, the articles (10) are conveyable at an angle, in particular transversely, with respect to one of (a) the conveying direction of the feed conveyor (19) and (b) substantially in the conveying direction of the grouping conveyor (12).

5. The device as claimed in claim 1, further comprising a shoulder (28) for articles (10) located in the region of the outside surface (26) of the conveyor (24) for the abutment of an edge of the articles (10) lying in front in the conveying direction when articles (10) are being supplied to the grouping conveyor (12).

6. The device as claimed in claim 1, wherein the circumferential speed of the rotatingly driven conveyor (24) is faster than the speed articles (10) are supplied.

7. The device as claimed in claim 1, further comprising a device for delivering an air flow (31) which acts on the articles (10) laterally in the conveying direction of the grouping conveyor (12)$_1$ is the device for delivering an air flow (31) being positioned in the operating region of the conveyor (24).

8. The device as claimed in claim 1, wherein articles (10) are conveyable in a stationary manner on a conveyor run (18) of the grouping conveyor (12), wherein the conveyor run (18) is set up to act upon articles (10) with negative pressure.

9. The device as claimed in claim 1, wherein, at least in the region of the of the feeding of the articles (10), the grouping conveyor (12) has a stop means (23) which is directed transversely with respect to the conveying direction of articles (10) on the feed conveyor (19), wherein the stop means (23) is set up to act upon articles (10) with negative pressure.

10. The device as claimed in claim 7, wherein an output-side end of the feed conveyor (19), the conveyor (24), and the device for delivering an air flow (31) are connected to form one unit which is movable as one and which is movable laterally parallel to the grouping conveyor (12).

11. The device as claimed in claim 8, wherein the compartments (13) formed on the grouping conveyor (12) are defined by entrainment means (16) of the conveyor run (18), wherein the articles (10) project beyond the top surface of the entrainment means (16) and the conveyor (24) is arranged above the entrainment means (16) for conveying articles (10).

12. The device as claimed in claim 11, wherein a top surface of the entrainment means (16) is positioned so as to be inclined in a descending manner on the grouping conveyor (12) in opposition to the direction in which articles (10) are supplied.

13. A method for grouping articles (10), in particular hygiene products such as diapers, comprising:

conveying articles (10) to be grouped individually and one after another on a feed conveyor (10);

supplying articles (10) to a substantially cone-shaped conveyor (24) mounted on the device at an angle;

driving the substantially cone-shaped conveyor (24) rotatingly about an upright axis of rotation (25) that is inclined with respect to the vertical about two axes;

supplying articles (10) into compartments (13) of a grouping conveyor (12) by way of the substantially cone-shaped conveyor (24), wherein the substantially cone-shaped conveyor (24) supplies articles (10) to the grouping conveyor (12) at an angle that is substantially transverse to the conveying direction of the grouping conveyor (12), whereby a portion of an outside surface (26) of the cone-shaped conveyor (24) against which articles (10) abut for conveying is directed substantially transversely with respect to the conveying path of articles (10) when conveying articles (10) into the compartments (13); and in each case supplying one group (11) of articles (10) to each of the compartments (13), in which compartments articles (10) are arranged standing upright, wherein a group (11) of articles (10) is formed in each of the compartments (13).

14. The method as claimed in claim 13, further comprising acting upon articles (10) in the operating region of the conveyor (24) with an air flow which acts on articles (10) laterally in the conveying direction of the grouping conveyor (12).

15. The method as claimed in claim 13, further comprising, in the region of the grouping conveyor (12), holding articles (10) on at least one of (a) a conveyor run (18) of the grouping conveyor (12) and (b) a lateral stop means (23) by means of negative pressure.

16. The method as claimed in claim 14, further comprising, in the region of the grouping conveyor (12), holding articles (10) on at least one of (a) a conveyor run (18) of the grouping conveyor (12) and (b) a lateral stop means (23) by means of negative pressure.

* * * * *